United States Patent [19]

Zinke

[11] 4,376,054
[45] Mar. 8, 1983

[54] 1,3,2-DIOXAPHOSPHOLANES AS LUBRICANT ADDITIVES AND LUBRICANTS CONTAINING SAME

[75] Inventor: Horst Zinke, Ernsthofen, Fed. Rep. of Germany

[73] Assignee: Ciba-Geigy Corporation, Ardsley, N.Y.

[21] Appl. No.: 311,690

[22] Filed: Oct. 15, 1981

Related U.S. Application Data

[63] Continuation of Ser. No. 164,641, Jun. 30, 1980, abandoned.

[30] Foreign Application Priority Data

Jul. 6, 1979 [CH] Switzerland .................. 6350/79

[51] Int. Cl.³ .................................................. C10M 1/48
[52] U.S. Cl. ................................. 252/46.7; 252/46.6; 260/927 R
[58] Field of Search ................... 252/46.6, 46.7; 260/927 R

[56] References Cited

U.S. PATENT DOCUMENTS

| | | | |
|---|---|---|---|
| 2,736,706 | 2/1956 | Morris | 252/46.6 |
| 2,900,407 | 8/1959 | Lanham | 252/46.6 X |
| 3,070,619 | 12/1962 | Lanham | 252/46.6 X |
| 3,135,694 | 6/1964 | Loughran et al. | 252/46.6 |
| 3,192,162 | 6/1965 | Bartlett et al. | 252/46.6 |
| 3,682,819 | 8/1972 | Morris et al. | 252/32.7 E |
| 3,687,848 | 8/1972 | Colclough et al. | 252/46.6 X |
| 3,795,612 | 3/1974 | Stournas et al. | 252/46.6 |
| 3,880,735 | 4/1975 | Oswald | 252/46.6 X |
| 4,244,827 | 1/1981 | Michaelis et al. | 252/46.4 |

OTHER PUBLICATIONS

Johnson, Chem. Abstracts, vol. 90, 1979, 5930 w, p. 544.

*Primary Examiner*—Andrew Metz
*Attorney, Agent, or Firm*—Luther A. R. Hall; Harry Falber

[57] ABSTRACT

1,3-Dioxaphospholanes of the formula

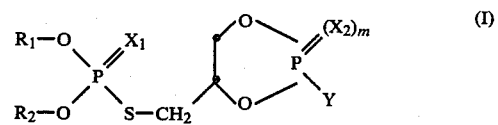

are suitable as high-pressure additives in natural and/or synthetic lubricating oils.

15 Claims, No Drawings

1,3,2-DIOXAPHOSPHOLANES AS LUBRICANT ADDITIVES AND LUBRICANTS CONTAINING SAME

This is a continuation of application Ser. No. 164,641 filed on June 30, 1980 now abandoned.

The present invention relates to novel 1,3,2-dioxaphospholanes, to their production and to their use as lubricant additives, and to the lubricating-oil formulations containing the novel compounds.

Various additives are in general added to mineral and synthetic lubricants in order to improve the performance characteristics of these lubricants. There is in particular a need for additives able to protect the devices to be lubricated from frictional wear. The requirement which wear inhibitors of this kind are expected to meet is that they increase the load-bearing capacity of the lubricant and do not have a corrosive action on the metal parts to be protected. The use of cyclic phosphorus compounds as additives for lubricating oils is known from the U.S. Pat. Nos. 3,192,162 and 3,682,819. Furthermore, there are known from the German Offenlegungsschrift No. 2,802,756 mixtures which can likewise contain cyclic phosphorus compounds as lubricating-oil additives.

There has now been found a novel class of substituted 1,3,2-dioxaphospholanes which, as ashless additives, are excellently effective as high-pressure additives for lubricants.

The novel compounds correspond to the general formula (I)

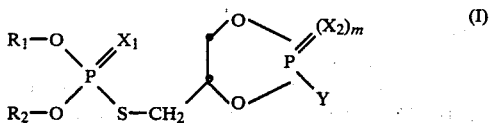

wherein $R_1$ and $R_2$ independently of one another are each $C_1$-$C_{18}$-alkyl, $C_5$-$C_{12}$-cycloalkyl, phenyl or $C_7$-$C_9$-aralkyl each of which is unsubstituted or is substituted by one or two $C_1$-$C_{12}$-alkyl groups, or $R_1$ and $R_2$ are each $C_2$-$C_{10}$-alkoxyalkyl or $C_3$-$C_{20}$-alkoxycarbonylalkyl, or $R_1$ and $R_2$ together form a bivalent radical of the formula II

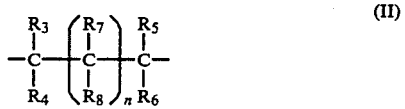

wherein $R_3$, $R_4$, $R_5$ and $R_6$ independently of one another are each hydrogen, $C_1$-$C_4$-alkyl, cyclohexyl or phenyl, and $R_7$ and $R_8$ independently of one another are each hydrogen, $C_1$-$C_4$-alkyl, cyclohexyl, phenyl, nitro, cyano, $C_2$-$C_{19}$-alkoxycarbonyl, $C_2$-$C_{18}$-alkanoyl, or a group of the formula $(R_9$—O$)_2$—P(O)—, in which $R_9$ is $C_1$-$C_{18}$-alkyl, or $R_7$ and $R_8$ together are 2-butenylene or 2-pentenylene, and n is nought or 1, and one of the radicals $X_1$ or $X_2$ is oxygen and, when $R_1$ and $R_2$ together are a radical of the formula II, also sulfur, and the other is oxygen or sulfur, and m is nought or 1, and Y is hydrogen, halogen, —$OR_{10}$ or —$SR_{10}$, in which $R_{10}$ is hydrogen, $C_1$-$C_{18}$-alkyl, $C_5$-$C_{12}$-cycloalkyl, phenyl or $C_7$-$C_9$-aralkyl each of which is unsubstituted or substituted by one or two $C_1$-$C_{12}$-alkyl groups and/or by a $C_3$-$C_{20}$-alkoxycarbonylalkyl group, or $R_{10}$ is $C_3$-$C_{10}$-alkoxyalkyl or $C_3$-$C_{20}$-alkoxycarbonylalkyl, or Y is —N($R_{11}$)$R_{12}$, —OH.NH$_3$, —SH.NH$_3$, —OH.($R_{11}$)N($R_{12}$)$R_{13}$ or —SH.($R_{11}$)N($R_{12}$)$R_{13}$, in which $R_{11}$, $R_{12}$ and $R_{13}$ independently of one another are hydrogen, $C_1$-$C_{30}$-alkyl, $C_1$-$C_{30}$-alkenyl or $C_1$-$C_{30}$-alkoxyalkyl, whereby at least one of the radicals $R_{11}$, $R_{12}$ and $R_{13}$ contains 1-30 C atoms.

The substituents $R_1$ and $R_2$ in the formula I can have identical or different meanings. Compounds in which $R_1$ and $R_2$ are identical are preferred.

As $C_1$-$C_{18}$-alkyl, $R_1$, $R_2$, $R_9$ and $R_{10}$ are for example: methyl, ethyl, n-propyl, isopropyl, n-butyl, sec-butyl, tert-butyl, n-hexyl, 2-ethylhexyl, 6-methylheptyl, n-octyl, straight-chain or branched-chain nonyl, decyl, dodecyl, tridecyl, tetradecyl or octadecyl. Preferred alkyl groups have 3-13 C atoms.

As $C_5$-$C_{12}$-cycloalkyl and particularly as $C_6$-$C_{10}$-cycloalkyl, $R_1$, $R_2$ and $R_{10}$ can be for example: cyclopentyl, cyclohexyl, cyclooctyl, cyclodecyl or cyclododecyl. Cyclohexyl is preferred.

When $R_1$, $R_2$ and $R_{10}$ are phenyl or $C_7$-$C_9$-aralkyl, these aromatic radicals can be substituted by one or two alkyl groups having 1-12 C atoms, preferably 1-9 C atoms. Examples of alkyl substituents of this kind are: methyl, ethyl, isopropyl, n-butyl, sec-butyl, tert-butyl, tert-amine, n-hexyl, n-octyl, 1,1,3,3-tetramethylbutyl or 1,1,3,3,5,5-hexamethylhexyl. If $R_{10}$ as phenyl is substituted by a $C_3$-$C_{20}$-alkoxycarbonylalkyl group, this can have the meanings given below as examples for $R_1$, $R_2$ and $R_{10}$. When $R_1$, $R_2$ and $R_{10}$ are $C_7$-$C_9$-aralkyl, they can be α,α-dimethylbenzyl, but preferably β-phenylethyl and in particular benzyl.

When $R_1$, $R_2$ and $R_{10}$ are $C_2$-$C_{10}$-alkoxyalkyl, the alkyl part can contain 1-3 C atoms and the alkoxy part can consist of 1-8 C atoms, for example methoxymethyl, ethoxymethyl, 2-methoxyethyl, 2-ethoxyethyl, 2-n-butoxyethyl, 3-n-butoxypropyl, 2-octoxyethyl or methoxypropyl. To be given special mention are compounds in which $R_1$, $R_2$ and $R_{10}$ as alkoxyalkyl contain 3-6 C atoms.

As $C_3$-$C_{20}$-alkoxycarbonylalkyl, wherein the alkyl moiety contains 1-3 C atoms and alkoxycarbonyl moiety 2-18 C atoms, $R_1$, $R_2$ and $R_{10}$ are for example: methoxycarbonylmethyl, propoxycarbonylmethyl, butoxycarbonylmethyl, octoxycarbonylmethyl, dodecoxycarbonylmethyl, octadecoxycarbonylmethyl, methoxycarbonylethyl, ethoxycarbonylethyl, octadecoxycarbonylethyl or methoxycarbonylpropyl. $R_1$, $R_2$ and $R_{10}$ as alkoxycarbonylalkyl preferably contain 4-10 C atoms.

One of the radicals $X_1$ and $X_2$, particularly $X_2$, is preferably oxygen and, when $R_1$ and $R_2$ together are a group of the formula II, also sulfur, and the other is oxygen or sulfur. $X_1$ is especially sulfur. In preferred compounds, $X_1$ is sulfur, $X_2$ is oxygen, and m is 1.

If $R_3$, $R_4$, $R_5$, $R_6$, $R_7$ and $R_8$ are $C_1$-$C_4$-alkyl, it is for example methyl, ethyl, n-propyl, isopropyl, n-butyl, sec-butyl or tert-butyl.

As $C_2$-$C_{19}$-alkoxycarbonyl, $R_7$ and $R_8$ are for example: methoxycarbonyl, ethoxycarbonyl, butoxycarbonyl, hexoxycarbonyl, octoxycarbonyl, dodecoxycarbonyl or octadecoxycarbonyl. Preferred alkoxycarbonyl groups contain 2-9 C atoms.

$R_7$ and $R_8$ as $C_2$-$C_{18}$-alkanoyl can be for example acetyl, butyryl, hexanoyl, octanoyl, dodecanoyl or octadecanoyl. $C_2$-$C_8$-alkanoyl groups are preferred.

n is preferably 1.

Among the meanings given above for Y, the groups —SR$_{10}$ and particularly —SH.(R$_{11}$)N(R$_{12}$)R$_{13}$ are to be emphasised. Preferred also are the ammonium salts which are derived from ammonia or from primary, secondary or tertiary amines.

As C$_1$–C$_{30}$-alkyl, R$_{11}$, R$_{12}$ and R$_{13}$ can be for example: alkenyl, alkoxyalkyl, for example methyl, ethyl, n-propyl, isopropyl, tert-butyl, amyl, hexyl, 1-methylpentyl, 2-ethylhexyl, branched-chain or straight-chain octyl, decyl, dodecyl, tridecyl, octadecyl, eicosyl, hexacosyl or triacontyl, or they can be 2-octenyl, oleyl, 2-oxaoctyl, 2-oxadecyl, 2-octadecyl or 2-oxahexacosyl. Preferably at least one of the radicals R$_{11}$, R$_{12}$ and R$_{13}$ contains 8–30 C atoms.

R$_{11}$, R$_{12}$ and R$_{13}$ together with the nitrogen atom to which they are bound form oil-soluble organic nitrogen bases. Examples of bases of this kind are: octylamine, (2-ethylhexyl)-amine, decylamine, dodecylamine, tetradecylamine, octadecylamine, methyloctylamine, didodecylamine, methyloctadecylamine, methyloctyldecylamine, (octoxyethyl)-amine, (dodecyloxyethyl)-amine, dodecyl-dimethylamine, hexydecyl-dimethylamine, octadecyldimethylamine, tridecyl-dimethylamine, decyl-dimethylamine, didodecyl-methylamine, methyl-butyl-dodecylamine, trioctylamine, dioctyl-methylamine, dodecylbenzyl-methylamine, methyl-dodecenylamine, heptadecyl-dimethylamine, dioctylmethylamine, nonyl-dimethylamine, tris-(tridecyl)-amine, tris-(dodecyl)-amine, tris-(octyl)-amine, methyl-butyl-hexadecylamine, 3,5-dimethyl-pyridine, 2-(ethylhexyl)-methyl-dodecylamine, (methyl-ethyl)-dodecylamine, methyl-butyl-dodecylamine, dimethyl-dodecylamine, hexadecyl-dimethylamine and tris-(dodecyl)-amine.

Many bases of this type are obtainable on the market as commercial amines or mixtures of amines, for example Primene (manufacturer Röhm and Haas), Genamine (manufacturer Hoechst), Adogene (manufacturer Li lachim) or fatty amines, such as amines of tall oil, coconut oil, soya bean oil or tallow oil.

Preferred compounds of the formula I are those wherein R$_1$ and R$_2$ independently of one another are such C$_3$–C$_{13}$-alkyl, C$_6$–C$_{10}$-cycloalkyl, phenyl or C$_7$–C$_8$-aralkyl each of which is unsubstituted or substituted by one or two C$_1$–C$_4$-alkyl groups, or R$_1$ and R$_2$ are each C$_3$–C$_6$-alkoxyalkyl or C$_4$–C$_{10}$-alkoxycarbonylalkyl, or R$_1$ and R$_2$ together form a radical of the formula II, in which R$_3$, R$_4$, R$_5$ and R$_6$ independently of one another are each hydrogen or C$_1$–C$_4$-alkyl, and R$_7$ and R$_8$ independently of one another are each hydrogen, C$_1$–C$_4$-alkyl, cyclohexyl, phenyl, nitro, C$_2$–C$_9$-alkoxycarbonyl or C$_2$–C$_8$-alkanoyl, or R$_7$ and R$_8$ together are 2-butenylene or 2-pentenylene, and n, m, X$_1$, X$_2$, Y, R$_{11}$, R$_{12}$ and R$_{13}$ have the meanings defined in the foregoing, whereby R$_{10}$ is hydrogen, C$_3$–C$_{13}$-alkyl, C$_6$–C$_{10}$-cycloalkyl, phenyl or benzyl each unsubstituted or substituted by one or two C$_1$–C$_9$-alkyl groups, or R$_{10}$ is C$_4$–C$_{10}$-alkoxycarbonylalkyl.

Particularly preferred compounds of the formula I are those wherein R$_1$ and R$_2$ independently of one another are each C$_3$–C$_{13}$-alkyl, cyclohexyl, or phenyl or benzyl each of which is unsubstituted or is substituted by one or two alkyl groups, or R$_1$ and R$_2$ together are a radical of the formula II in which R$_3$, R$_4$, R$_5$ and R$_6$ independently of one another are each hydrogen or methyl, and R$_7$ and R$_8$ independently of one another are each hydrogen, C$_1$–C$_4$-alkyl, nitro, C$_2$–C$_9$-alkoxycarbonyl or C$_2$–C$_8$-alkanoyl, or R$_7$ and R$_8$ together are 2-butenylene or 2-pentenylene, and n is 1, X$_1$ is sulfur, X$_2$ is oxygen, m is 1, and Y has the above-given meaning, whereby R$_{10}$ is hydrogen, C$_3$–C$_{13}$-alkyl, cyclohexyl, phenyl or benzyl each of which is unsubstituted or is substituted by one or two C$_1$–C$_9$-alkyl groups, or R$_{10}$ is C$_4$–C$_{10}$-alkoxycarbonylalkyl, R$_{11}$, R$_{12}$ and R$_{13}$ independently of one another are each hydrogen, C$_{13}$–C$_{26}$-alkyl or C$_{13}$–C$_{26}$-alkyl or C$_{13}$–C$_{26}$-alkoxyalkyl, with at least one of the radicals R$_{11}$, R$_{12}$ or R$_{13}$ having 13–26 C atoms.

Of particular interest are compounds of the formula I wherein R$_1$ and R$_2$ are each C$_1$–C$_{18}$-alkyl, C$_5$–C$_{12}$-cycloalkyl, phenyl or C$_7$–C$_9$-aralkyl each of which is unsubstituted or is substituted by one or two C$_1$–C$_{12}$-alkyl groups, or R$_1$ and R$_2$ are each C$_3$–C$_{10}$-alkoxyalkyl or C$_3$–C$_{20}$-alkoxycarbonylalkyl, and the remaining symbols have the meanings defined in the foregoing.

Examples of compounds of the formula I to be mentioned are:

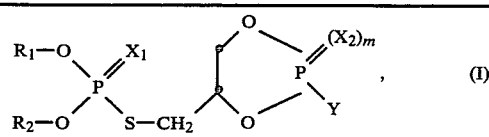

| No. | R$_1$ | R$_2$ | X$_1$ | X$_2$ | m | Y |
| --- | --- | --- | --- | --- | --- | --- |
| 1 | C$_{12}$H$_{25}$ | —C$_{12}$H$_{25}$ | S | O | 1 | —SH.N(C$_8$H$_{17}$)$_3$ |
| 2 | —C$_6$H$_5$ | —C$_4$H$_9$ | S | O | 1 | —OC$_6$H$_5$ |
| 3 | —C$_3$H$_7$ | —C$_3$H$_7$ | S | S | 1 | —SH.NH$_3$ |
| 4 | —C$_{13}$H$_{27}$ | —C$_{13}$H$_{27}$ | S | — | 0 | —NH(C$_{12}$H$_{25}$) |
| 5 | —C$_8$H$_{17}$ | —C$_8$H$_{17}$ | S | O | 1 | —S—⟨H⟩ |
| 6 | —C$_4$H$_9$ | —C$_4$H$_9$ | S | O | 1 | —SH.NH$_3$ |
| 7 | i-C$_8$H$_{17}$ | iC$_8$H$_{17}$ | S | — | 0 | —Cl |

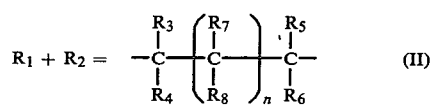

-continued

| Nr. | $R_3$ | $R_4$ | $R_5$ | $R_6$ | $R_7$ | $R_8$ | n | $X_1$ | $X_2$ | m | Y |
|---|---|---|---|---|---|---|---|---|---|---|---|
| 8  | H   | H   | H   | H   | —NO$_2$          | —C$_2$H$_5$            | 1 | S | S | 1 | —SH.N(C$_8$H$_{17}$)$_3$ |
| 9  | H   | H   | CH$_3$ | H   | —COOC$_2$H$_5$   | —COOC$_2$H$_5$         | 1 | S | O | 1 | —SH.NH$_3$ |
| 10 | H   | H   | H   | H   | —COOC$_8$H$_{17}$ | —CH$_3$               | 1 | S | O | 1 | —OH |
| 11 | H   | CH$_3$ | H | CH$_3$ | —COOC$_4$H$_9$  | —CH$_3$                | 1 | S | O | 1 | —SH.NH$_2$(C$_{12}$H$_{25}$) |
| 12 | H   | CH$_3$ | H | CH$_3$ | —               | —                       | 0 | S | O | 1 | —SH.NH$_3$ |
| 13 | H   | H   | H   | C$_4$H$_9$ | —          | —                       | 0 | S | O | 1 | —OCH$_2$OCOC$_4$H$_9$ |
| 14 | H   | H   | H   | H   | —COOiC$_8$H$_{17}$ | —P(O)(OC$_2$H$_5$)$_2$ | 1 | S | — | 0 | —S—CH$_2$COOiC$_8$H$_{17}$ |
| 15 | CH$_3$ | H | CH$_3$ | H | CN              | —COOC$_2$H$_5$          | 1 | S | S | 1 | —N(C$_{13}$H$_{27}$)$_2$ |
| 16 | CH$_3$ | CH$_3$ | H | CH$_3$ | H           | H                       | 1 | S | S | 1 | —H |

The method which can be adopted for the preparation of the compounds of formula I is known per se, and can comprise for example the reaction of a compound of the formula III $$R_1-O\diagdown \overset{X_1}{\underset{\diagup}{P}}\diagdown_{S-CH_2}\diagup^{O}\diagdown_{O}\diagup P-Cl, \quad (III)$$

wherein $R_1$, $R_2$ and $X_1$ have the meanings given above, with approximately the equimolar amount of a compound of the formula HY (IV). In the formula IV, the symbol Y has the above-given meaning. In the resulting products of the formula I wherein m is nought, oxygen or sulfur, corresponding to the meaning of $X_2$, can be optionally introduced by known methods. The compounds thus obtained correspond to the formula I in which m is 1, and the remaining symbols have the meanings given above.

The compounds of the formula III can be produced, in a manner known per se, by the reaction of diols of the formula V $$R_1-O\diagdown \overset{X_1}{\underset{\diagup}{P}}\diagdown_{S-CH_2}\diagup^{OH}\diagdown_{OH,}$$  (V)

wherein $R_1$, $R_2$ and $X_1$ have the meanings defined above, with approximately the equimolar amount of PCl$_3$. The compounds of the formula V can be produced from compounds of the formula VI, or from the ammonium salts thereof, $$R_1-O\diagdown \overset{X_1}{\underset{\diagup}{P}}\diagdown_{SH}$$  (VI)

wherein $R_1$, $R_2$ and $X_1$ have the above-given meanings, and epoxypropanol.

An alternative method for producing the compounds of the formula I comprises the reaction of compounds of the formula V with PX$_2$Cl$_3$, wherein X$_2$ has the meaning given above, and subsequent reaction of the reaction products with a compound of the formula IV. In the products of the formula I which are produced in this manner, m is 1, and the remaining symbols are as defined in the foregoing.

The compounds of the formulae IV and VI are known or, in the case where they are new, they can be produced by methods analogous to known methods.

Novel intermediates of the formulae IV and VI thus likewise form subject matter of the present invention.

An isolation of any of the intermediates is not necessary.

Even in very small amounts, the compounds of the formula I are effective as high-pressure additives in lubricants. Thus, mineral and synthetic lubricating oil, as well as mixtures thereof, which contain 0.001 to 5 percent by weight, preferably 0.02 to 3 percent by weight, relative to the lubricant, of a compound of the formula I have excellent high-pressure lubricating properties, which are clearly demonstrated by greatly reduced wear phenomena on the parts to be lubricated. The lubricants concerned are commonly known to one skilled in the art, and are described for example in the "Schmiermittel Taschenbuch" ("Lubricants Handbook") (Hüthig Verlag, Heidelberg, 1974).

The lubricating oil formulation can additionally contain other additives which are added in order to improve certain basic oil properties, for example additives such as antioxidants, metal passivators, rust inhibitors, agents for improving the viscosity index, pour-point depressors, dispersants/detergents, and other additives which protect against wear.

Examples of antioxidants are:

(a) alkylated and non-alkylated aromatic amines and mixtures thereof, for example: dioctyldiphenylamine, mono-t-octylphenyl-α- and -β-naphthylamines, phenothiazine, dioctylphenothiazine, phenyl-α-naphthylamine and N,N'-di-sec-butyl-p-phenylenediamine;

(b) sterically hindered phenols, for example: 2,6-di-tert-butyl-p-cresol, 4,4'-bis-(2,6-diisopropylphenol), 2,4,6-triisopropylphenol, 2,2'-thio-bis-(4-methyl-6-tert-butylphenol) and 4,4'-methylene-bis-(2,6-di-tert-butylphenol);

(c) alkyl phosphites, aryl phosphites or alkaryl phosphites, for example: trinonyl phosphite, triphenyl phosphite and diphenyldecyl phosphite;

(d) esters of thiodipropionic acid or thiodiacetic acid, for example: dilauryl thiodipropionate or dioctyl thiodiacetate;

(e) salts of carbamic and dithiophosphoric acids, for example: antimony diamyldithiocarbamate and zinc diamyldithiophosphate; and (f) combinations of two or more antioxidants from the above, for example: an alkylated amine and a sterically hindered phenol.

Examples of metal passivators are:

(a) for copper, for example: benzotriazole, tetrahydrobenzotriazole, 2-mercaptobenzothiazole, 2,5-dimercaptothiadiazole, salicylidene-propylenediamine and salts of salicylaminoguanidine;

(b) for lead, for example: sebacic acid derivatives, quinizarine and propyl gallate; and (c) a combination of two or more of the above additives.

Examples of rust inhibitors are:

(a) organic acids and their esters, metal salts and anhydrides, for example: N-oleoyl-sarcosine, sorbitane monooleate, lead naphthenate and dodecenylsuccinic anhydride;

(b) nitrogen-containing compounds, for example:
I. primary, secondary or tertiary aliphatic or cycloaliphatic amines and amine salts of organic and inorganic acids, for example oil-soluble alkyl-ammonium carboxylates, and
II. heterocyclic compounds, for example: substituted imidazolines and oxazolines;

(c) phosphorus-containing compounds, for example: amine salts of phosphoric acid partial esters;

(d) sulfur-containing compounds, for example: barium dinonylnaphthalene-sulfonates and calcium petroleum sulfonates; and (e) combinations of two or more of the above additives.

Examples of agents which improve the viscosity index are for example: polymethacrylates, vinylpyrrolidone/methacrylate copolymers, polybutenes, olefine copolymers and styrene/acrylate copolymers.

Examples of pour-point depressors are for example: polymethacrylates and alkylated naphthalene derivatives.

Examples of dispersants/detergents are for example: polybutenylsuccinic acid imides, polybutenylphosphonic acid derivatives and hyperbasic sulfonates and phenolates of magnesium, calcium and barium.

Examples of other additives which provide protection against wear are for example: compounds which contain sulfur and/or phosphorus and/or halogen, such as vegetable oils treated with sulfur, zinc dialkyldithiophosphates, tritolyl phosphate, chlorinated paraffins, alkyl disulfides and aryl disulfides.

The Examples which follow illustrate the invention.

EXAMPLE 1 tert-Dodecyl-tetradecylammonium-2-oxo-2-thiol-4-(diisooctyloxythiophosphoryl-thiomethyl-1,3,2-dioxaphospholane 14.82 g (0.20 mol) of freshly distilled 2,3-epoxypropanol were added with stirring, in the course of half an hour, to a solution of 70.92 g (0.20 mol) of dithiophosphoric acid-0,0-di-2-ethylhexyl ester in 100 ml of toluene, and the mixture was subsequently stirred for half an hour at 65°–70° C.

The addition product obtained was cyclised, without intermediate isolation, with 27.46 g (0.20 mol) of phosphorus trichloride, under hydrogen chloride, to give phosphorus acid diester chloride, and this was further reacted with 3.6 g (0.2 mol) of water in 6.4 ml of dioxane to the corresponding 2-oxo-(2H)-1,3,2-dioctaphospholane.

To the toluene solution of the product obtained were subsequently added, with stirring, 4.41 g (0.20 mol) of sulfur and 40.3 g (0.20 mol) of a primary tert-dodecyl/tetradecylamine mixture (neutral equivalent 201.5), and the whole was stirred for 2 hours at 50° C. After cooling of the reaction mixture, it was washed with water and 5% sodium sulfate solution and dried with sodium sulfate, and the solvent was distilled off in vacuo. The product obtained was in the form of a viscous yellow liquid; $n_D^{20} = 1.5048$; acid number: calculated 79.5, found 86.1.

| | Analysis: | | | | |
|---|---|---|---|---|---|
| | % C | % H | % N | % P | % S |
| calculated: | 54.4 | 9.9 | 2.0 | 8.8 | 13.6 |
| found: | 54.1 | 9.8 | 2.1 | 8.5 | 13.2 |

The following compounds were synthesised according to Example 1.

TABLE 6

| Example | Compound | $n_D^{20}$ | Analysis % N | Calculated/Found % P |
|---|---|---|---|---|
| 2 | Di-(isooctyl)ammonium-2,2-oxo-thiol-4-(diisooctyloxy-thiophosphoryl-thiomethyl)-1,3,2-dioxaphospholane | 1.4992 | 1.9 / 2.1 | 8.3 / 8.2 |
| 3 | Prim.-(octadecyl-docosyl)-ammonium-2,2-oxo-thiol-4-(diisooctyloxy-thiophosphoryl-thiomethyl)-1,3,2-dioxaphospholane | 1.5050 | 2.1 / 1.9 | 9.3 / 8.4 |
| 4 | Di-(tridecyl)ammonium-2,2-oxo-thiol-4-(diisooctyloxy-thiophosphoryl-thiomethyl)-1,3,2-dioxaphospholane | 1.4932 | 1.6 / 1.8 | 7.0 / 6.8 |
| 5 | Di-(tridecyl)ammonium-2,2-thiono-thiol-4-(2'-thiono-5'-ethyl-5'-butyl-1',3',2,-dioxaphosphorinon-2'-yl-2'-thiomethyl)-1,3,2-dioxaphospholane | 1.5161 | 1.7 / 1.8 | 7.7 / 7.6 |

EXAMPLE 6

2-Thio-2-octyloxycarbonylmethylthio-4-(diisooctyloxythiophosphoryl-thiomethyl)-1,3,2-dioxaphospholane To the cyclic phosphorous acid diester chloride obtained according to Example 1 from 70.9 g (0.2 mol) of dithiophosphoric acid-0,0-diisooctyl ester by addition reaction with 14.8 g (0.2 mol) of 2,3-epoxypropanol, and subsequent reaction with 27.5 g (0.2 mol) of phosphorus trichloride, was added in the course of one hour, at a temperature of below 10° C., a mixture of 40.9 g of thioglycolic acid-isooctyl ester and 21.2 g (0.21 mol) of triethylamine in toluene, and the mixture was stirred for one hour at room temperature and subsequently for one hour at 45°–50° C.

The triethylamine hydrochloride which had precipitated was filtered off, and the solvent was distilled off in vacuo. A filtering auxiliary was added to the residue and filtration was carried out. The product obtained was in the form of a colourless liquid; $n_D^{20} = 1.4983$.

| | Analysis: | | | |
|---|---|---|---|---|
| | % C | % H | % P | % S |
| calculated: | 52.7 | 8.9 | 9.4 | 14.6 |
| found: | 52.5 | 8.9 | 9.3 | 14.4 |

EXAMPLES 8 TO 36

The compounds listed below were produced in a manner analogous to that of Examples 1 and 6

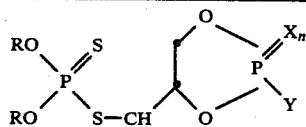

| No. | R | n | X | Y | $n_D^{20}$ | % P Calc. | % P found |
|---|---|---|---|---|---|---|---|
| 8 | n-C$_4$H$_9$— | 1 | S | —OH.HN(iC$_8$H$_{17}$)$_2$ | 1.5076 | 9.7 | 9.6 |
| 9 | n-C$_4$H$_9$— | 1 | S | —OH.HN(iC$_{13}$H$_{27}$)$_2$ | 1.4986 | 8.0 | 7.9 |
| 10 | n-C$_{12}$H$_{25}$— | 1 | S | —OH.HN(iC$_8$H$_{17}$)$_2$ | 1.4944 | 7.2 | 6.9 |
| 11 | C$_9$H$_{19}$—C$_6$H$_4$— | 1 | S | —OH.HN(iC$_8$H$_{17}$)$_2$ | 1.5300 | 6.7 | 6.4 |
| 12 | iC$_3$H$_7$— | 1 | S | —N(iC$_{13}$H$_{27}$)$_2$ | 1.4970 | 8.5 | 8.0 |
| 13 | iC$_3$H$_7$ | 1 | S | —O—C$_{10}$H$_{21}$ | 1.5044 | 12.2 | 11.8 |
| 14 | iC$_3$H$_7$— | 0 | — | —S—CH$_2$—C(=O)—O—C$_{10-16}$H$_{21-33}$ | 1.5001 | 10.5 | 9.9 |
| 15 | iC$_3$H$_7$— | 1 | S | —O—C$_6$H$_4$—C$_9$H$_{19}$ | 1.5281 | 10.9 | 10.0 |
| 16 | iC$_3$H$_7$— | 0 | — | —O—C$_6$H$_2$X$_2$—CH$_2$CH$_2$—CO$_2$CH$_3$ | 1.5253 | 10.2 | 9.9 |
| 17 | iC$_3$H$_7$— | 1 | S | —O—C$_6$H$_4$—CH$_3$CH$_2$CO$_2$CH$_3$ | 1.5332 | 9.7 | 9.2 |
| 18 | iC$_4$H$_9$— | 1 | S | —N(C$_2$H$_5$)$_2$ | 1.5260 | 13.8 | 13.5 |
| 19 | iC$_4$H$_9$— | 1 | S | —N(morpholino) | 1.5350 | 13.4 | 13.1 |
| 20 | iC$_4$H$_9$— | 1 | S | —O—C$_6$H$_5$ | 1.5367 | | |
| 21 | C$_5$H$_{11}$— | 1 | S | —O—C$_5$H$_{11}$ | 1.5098 | 12.6 | 12.4 |
| 22 | C$_5$H$_{11}$— | 1 | S | —O—C$_6$H$_4$—C$_9$H$_{19}$ | 1.5228 | 9.9 | 9.1 |
| 23 | iC$_8$H$_{17}$— | 0 | — | —N(iC$_8$H$_{17}$)$_2$ | 1.4883 | 8.9 | 8.7 |
| 24 | iC$_8$H$_{17}$— | 1 | S | —N(iC$_8$H$_{17}$)$_2$ | 1.4990 | 8.5 | 8.2 |
| 25 | iC$_8$H$_{17}$— | 0 | — | —N(iC$_{13}$H$_{27}$)$_2$ | 1.4868 | 7.4 | 7.3 |
| 26 | iC$_8$H$_{17}$— | 1 | S | —N(iC$_{13}$H$_{27}$)$_2$ | 1.4947 | 7.1 | 7.0 |
| 27 | iC$_{13}$H$_{27}$— | 0 | — | —N(C$_2$H$_5$)$_2$ | 1.4946 | 9.2 | 9.1 |
| 28 | iC$_{13}$H$_{27}$— | 1 | S | —N(C$_2$H$_5$)$_2$ | 1.5032 | 8.8 | 8.9 |
| 29 | iC$_{13}$H$_{27}$— | 0 | — | —N(morpholino) | 1.5001 | 9.1 | 9.0 |
| 30 | iC$_{13}$H$_{27}$ | 1 | S | —N(piperidino) | 1.5082 | 8.7 | 8.6 |
| 31 | iC$_{13}$H$_{27}$— | 0 | — | —N(2-methylimidazolyl) | 1.5010 | 9.1 | 9.2 |

-continued

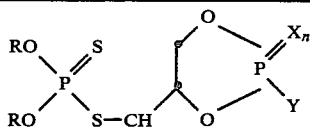

| No. | R | n | X | Y | $n_D^{20}$ | % P Calc. | % P found |
|---|---|---|---|---|---|---|---|
| 32 | iC$_{13}$H$_{27}$ | 1 | S | (pyrazole with N–CH$_3$) | 1.5157 | 8.7 | 8.8 |
| 33 | iC$_{13}$H$_{27}$— | 0 | — | —O—iC$_4$H$_9$ | 1.4890 | 9.2 | 9.0 |
| 34 | iC$_{13}$H$_{27}$ | 1 | S | —O—iC$_4$H$_9$ | 1.4966 | 8.8 | 8.4 |
| 35 | C$_9$H$_{19}$—phenyl | 1 | S | —O—CH$_3$ | 1.5491 | 8.8 | 8.1 |
| 36 | C$_9$H$_{19}$—phenyl | 1 | S | —N(C$_2$H$_5$)$_2$ | 1.5491 | 8.4 | 7.9 |

EXAMPLE 37

In order to determine the load-bearing capacity and anti-wear properties of the compounds listed below, these were incorporated into a non-doped mineral lubricating oil and tested in a Shell four-ball apparatus according to DIN 51350 (=IP 239/69). By way of comparison, a test was made also on the non-doped mineral lubricating oil without additive.

TABLE 1

| Test No. | Additive according to Example No. | Conc. (%) | ISL[1] (kg) | WL[2] (kg) | WSD[3] (mm) |
|---|---|---|---|---|---|
| 1[+] | no additive | — | 80 | 160 | 0,86 |
| 2 | 6 | 1,0 | 140 | 240 | 0,3 |
| 3 | 2 | 1,0 | 180 | 260 | 0,3 |
| 4 | 3 | 1,0 | 180 | 280 | 0,4 |
| 5 | 5 | 1,0 | 110 | 260 | 0,3 |
| 6 | 23 | 1,0 | 140 | 200 | 0.4 |
| 7 | 24 | 1,0 | 120 | 200 | 0.43 |
| 8 | 30 | 1,0 | 130 | 220 | 0.78 |
| 9 | 34 | 1,0 | 120 | 200 | 0.55 |

[+] non-doped mineral lubricating oil
[1] I.S.L. = Initial Seizure Load: that is the load under which the oil film breaks down within a duration of load application of 10 seconds;
[2] W.L. = Weld Load: that is the load under which the 4 balls weld together within 10 seconds;
[3] W.S.D. = Wear Scar Diameter in mm: that is the mean wear diameter when a load of 40 kg is applied for 1 hour.

What is claimed is:
1. A compound of formula I

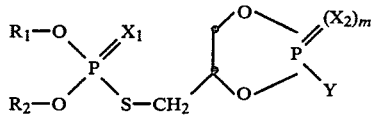

wherein R$_1$ and R$_2$ independently of one another are each C$_1$–C$_{18}$-alkyl, C$_5$–C$_{12}$-cycloalkyl, phenyl, phenyl substituted by one or two C$_1$–C$_{12}$ alkyl groups, C$_7$–C$_9$ aralkyl, C$_7$–C$_9$ aralkyl substituted by one or two C$_1$–C$_{12}$ alkyl groups; or R$_1$ and R$_2$ are each C$_2$–C$_{10}$ alkoxyalkyl, C$_3$–C$_{20}$ alkoxycarbonylalkyl; or R$_1$ and R$_2$ together form a bivalent radical of the formula II $$-\underset{R_4}{\overset{R_3}{C}}-\left(\underset{R_8}{\overset{R_7}{C}}\right)_n-\underset{R_6}{\overset{R_5}{C}}-\qquad (II)$$

wherein R$_3$, R$_4$, R$_5$ and R$_6$ independently of one another are each hydrogen, C$_1$–C$_4$-alkyl, cyclohexyl or phenyl, R$_7$ and R$_8$ independently of one another are each hydrogen, C$_1$–C$_4$-alkyl, cyclohexyl, phenyl, nitro, cyano, C$_2$–C$_{19}$-alkoxycarbonyl, C$_2$–C$_{18}$-alkanoyl, a group of the formula (R$_9$—O)$_2$—P(O)—, in which R$_9$ is C$_1$–C$_{18}$-alkyl, or R$_7$ and R$_8$ together are 2-pentenylene or 2-butenylene, n is nought or 1, one of the radicals X$_1$ or X$_2$ is oxygen and the other is oxygen or sulfur, with the proviso that X$_1$ and X$_2$ independently can either be oxygen or sulfur when R$_1$ and R$_2$ together are a radical of formula II, m is nought or 1, and Y is hydrogen, halogen, —OR$_{10}$, —SR$_{10}$, —N(R$_{11}$)R$_{12}$, —OH.NH$_3$, —SH.NH$_3$, OH.(R$_{11}$)N(R$_{12}$)R$_{13}$ or —SH.(R$_{11}$)N(R$_{12}$)R$_{13}$, in which R$_{10}$ is hydrogen, C$_1$–C$_{18}$ alkyl, C$_5$–C$_{12}$ cycloalkyl, phenyl, phenyl substituted by one or two C$_1$–C$_{12}$ alkyl groups, phenyl substituted by a C$_3$–C$_{20}$ alkoxycarbonylalkyl group or phenyl substituted by a mixture of alkyl and alkoxycarbonylalkyl groups; C$_7$–C$_9$ aralkyl, C$_7$–C$_9$ aralkyl substituted by one or two C$_1$–C$_{12}$ alkyl groups, C$_7$–C$_9$ aralkyl substituted by a C$_3$–C$_{20}$ alkoxycarbonylalkyl group or C$_7$–C$_9$ aralkyl substituted by a mixture of alkyl and alkoxycarbonylalkyl groups; C$_3$–C$_{10}$ alkoxyalkyl or C$_3$–C$_{20}$ alkoxycarbonylalkyl, and R$_{11}$, R$_{12}$ and R$_{13}$ independently of one another are each hydrogen, C$_1$–C$_{30}$-alkyl, C$_1$–C$_{30}$-alkenyl or C$_1$–C$_{30}$-alkoxyalkyl, whereby at least one of the radicals R$_{11}$, R$_{12}$ and R$_{13}$ contains 1–30 C atoms.

2. A compound according to claim 1 wherein R$_1$ and R$_2$ independently of one another are each C$_3$–C$_{13}$ alkyl, C$_6$–C$_{10}$ cycloalkyl, phenyl, phenyl substituted by one or two C$_1$–C$_4$ alkyl groups, C$_7$–C$_8$ aralkyl, C$_7$–C$_8$ aralkyl substituted by one or two C$_1$–C$_4$ alkyl groups; or R$_1$ and $R_2$ are each $C_3$–$C_6$ alkoxyalkyl, $C_4$–$C_{10}$ alkoxycarbonylalkyl; or $R_1$ and $R_2$ together form a radical of the formula II, in which $R_3$, $R_4$, $R_5$ and $R_6$ independently of one another are each hydrogen or $C_1$–$C_4$-alkyl, and $R_7$ and $R_8$ independently of one another are each hydrogen, $C_1$–$C_4$-alkyl, cyclohexyl, phenyl, nitro, $C_2$–$C_9$-alkoxycarbonyl, $C_2$–$C_8$-alkanoyl, or $R_7$ and $R_8$ together are 2-butenylene or 2-pentenylene, and $R_{10}$ is hydrogen, $C_3$–$C_{13}$ alkyl, $C_6$–$C_{10}$ cycloalkyl, phenyl, phenyl substituted by one or two $C_1$–$C_9$ alkyl groups, benzyl, benzyl substituted by one or two $C_1$–$C_9$ alkyl groups or $C_4$–$C_{10}$ alkoxycarbonylalkyl.

3. A compound according to claim 1 wherein $R_1$ and $R_2$ independently of one another are each $C_3$–$C_{13}$ alkyl, cyclohexyl, phenyl, phenyl substituted by one or two $C_1$–$C_4$ alkyl groups, benzyl, benzyl substituted by one or two $C_1$–$C_4$ alkyl groups, or $R_1$ and $R_2$ together are a radical of the formula II in which $R_3$, $R_4$, $R_5$ and $R_6$ independently of one another are each hydrogen or methyl, $R_7$ and $R_8$ independently of one another are each hydrogen, $C_1$–$C_4$-alkyl, nitro, $C_2$–$C_9$-alkoxycarbonyl, $C_2$–$C_8$-alkanoyl, or $R_7$ and $R_8$ together are 2-pentenylene or 2-butenylene, n is 1, $X_1$ is sulfur, $X_2$ is oxygen, m is 1, $R_{10}$ is hydrogen, $C_3$–$C_{13}$ alkyl, cyclohexyl, phenyl, phenyl substituted by one or two $C_1$–$C_9$ alkyl groups, benzyl, benzyl substituted by one or two $C_1$–$C_9$ alkyl groups, or $C_4$–$C_{10}$-alkoxycarbonylalkyl, and $R_{11}$, $R_{12}$ and $R_{13}$ independently of one another are each hydrogen, $C_1$–$C_{26}$-alkyl or $C_1$–$C_{26}$-alkoxyalkyl, with at least one of the radicals $R_{11}$, $R_{12}$ or $R_{13}$ having 13–26 C atoms.

4. A compound according to claim 1 wherein $R_1$ and $R_2$ together form a radical of formula II in which n is 1.

5. A compound according to claim 1 wherein $R_1$ and $R_2$ are each $C_1$–$C_{18}$ alkyl, $C_5$–$C_{12}$ cycloalkyl, phenyl, phenyl substituted by one or two $C_1$–$C_{12}$ alkyl groups, $C_7$–$C_9$ aralkyl, $C_7$–$C_9$ aralkyl substituted by one or two $C_1$–$C_{12}$ alkyl groups, $C_3$–$C_{10}$ alkoxyalkyl or $C_3$–$C_{20}$ alkoxycarbonylalkyl.

6. The compound according to claim 1 (tert-dodecyl-tetradecyl)ammonium-2-oxo-2-thiol-4-(diisooctyloxy-thiophosphorylthiomethyl)-1,3,2-dioxaphospholane.

7. The compound according to claim 1 di-(isooctyl)-ammonium-2-oxo-2-thiol-4-(diisooctyloxythiophosphoryl-thiomethyl)-1,3,2-dioxaphospholane.

8. The compound according to claim 1 (octadecyldocosyl)ammonium-2-oxo-2-thiol-4-(diisooctyloxythiophosphoryl-thiomethyl)-1,3,2-dioxaphospholane.

9. The compound according to claim 1 di(tridecyl)-ammonium-2-thiono-2-thiol-4-(2-thiono-5-ethyl-5-butyl-1,3,2-dioxaphosphorinon-2-yl-thiomethyl)-1,3,2-dioxaphospholane.

10. The compound according to claim 1 2-di(isooctyl)-amino-4-(diisooctyloxythiophosphoryl-thiomethyl)-1,3,2-dioxaphospholane.

11. The compound according to claim 1 2-isooctyloxycarbonylmethylthio-4-(diisooctyloxythiophosphoryl-thiomethyl)-1,3,2-dioxaphospholane.

12. A compound of the formula I according to claim 1 wherein one of the radicals $X_1$ and $X_2$ is oxygen and the other is oxygen or sulfur.

13. A compound of the formula I according to claim 1 wherein $X_1$ is sulfur, $X_2$ is oxygen, and m is 1.

14. A compound of the formula I according to claim 1 wherein Y is —$SR_{10}$ or —$SH.(R_{11})N(R_{12})R_{13}$.

15. A lubricant composition comprising a lubricating oil containing 0.001 to 5 percent, relevant to the oil, of a compound of formula I according to claim 1.

* * * * *